(12) United States Patent
Yao et al.

(10) Patent No.: US 10,873,218 B2
(45) Date of Patent: Dec. 22, 2020

(54) SYNCHRONIZED TIME-DIVISION WIRELESS POWER TRANSFER FOR MULTIPLE VOLTAGE APPLICATIONS

(71) Applicant: AGENCY FOR SCIENCE, TECHNOLOGY AND RESEARCH, Singapore (SG)

(72) Inventors: Lei Yao, Singapore (SG); Jia Hao Cheong, Singapore (SG); Yuan Gao, Singapore (SG)

(73) Assignee: Agency for Science, Technology and Research, Singapore (SG)

(*) Notice: Subject to any disclaimer, the term of this patent is extended or adjusted under 35 U.S.C. 154(b) by 0 days.

(21) Appl. No.: 16/095,678

(22) PCT Filed: Apr. 20, 2017

(86) PCT No.: PCT/SG2017/050222
§ 371 (c)(1),
(2) Date: Oct. 22, 2018

(87) PCT Pub. No.: WO2017/184083
PCT Pub. Date: Oct. 26, 2017

(65) Prior Publication Data
US 2019/0207424 A1    Jul. 4, 2019

(30) Foreign Application Priority Data

Apr. 22, 2016 (SG) .............. 10201603240Y

(51) Int. Cl.
*H02J 50/12* (2016.01)
*H02J 50/80* (2016.01)
(Continued)

(52) U.S. Cl.
CPC .......... *H02J 50/12* (2016.02); *A61B 5/0031* (2013.01); *H02J 50/80* (2016.02); *H02M 1/00* (2013.01); *H02M 3/04* (2013.01)

(58) Field of Classification Search
CPC ....... H02J 50/10; H02J 50/12; A61B 1/00029; A61N 1/3787
(Continued)

(56) References Cited

U.S. PATENT DOCUMENTS 7,256,568 B2 * 8/2007 Lam .................. H02M 1/10
                                                323/222
7,657,320 B2 * 2/2010 Chadwick ............ H01Q 1/44
                                                607/60

(Continued)

FOREIGN PATENT DOCUMENTS

| JP | 2014-79091 A | 5/2014 |
| WO | WO 2015/080539 A1 | 6/2015 |
| WO | WO 2015/177905 A1 | 11/2015 |

OTHER PUBLICATIONS

PCT International Search Report for PCT Counterpart Application No. PCT/SG20167/050222 Containing International Search Report, 3 pgs. (dated Jul. 14, 2017).

(Continued)

*Primary Examiner* — Rexford N Barnie
*Assistant Examiner* — Joseph N Inge
(74) *Attorney, Agent, or Firm* — Womble Bond Dickinson (US) LLP

(57) ABSTRACT

A wirelessly powered implantable medical device, a system for synchronized time-division wireless power transfer, and a method for closed-loop carrier waveform adaption for wireless power control are provided. The system for synchronized time-division wireless power transfer includes a wireless transmitter for generating and transmitting time-division wireless power transfer signals and a wirelessly (Continued)

powered device. The wirelessly powered device includes a wireless receiver for receiving the time-division wireless power transfer signals and a time division switching module. The time division switching module is coupled to the wireless receiver and generates multiple supply voltages synchronized to the time-division wireless power transfer signals for powering different circuitry of the wirelessly powered device.

11 Claims, 6 Drawing Sheets

(51) Int. Cl.
*A61B 5/00* (2006.01)
*H02M 1/00* (2006.01)
*H02M 3/04* (2006.01)

(58) Field of Classification Search
USPC .......................................................... 307/104
See application file for complete search history.

(56) References Cited

U.S. PATENT DOCUMENTS

| | | | | |
|---|---|---|---|---|
| 9,520,724 | B2* | 12/2016 | Anttila | H02J 7/00047 |
| 9,692,296 | B1* | 6/2017 | Dash | H02M 3/04 |
| 2010/0114216 | A1* | 5/2010 | Krause | A61N 1/37288 |
| | | | | 607/5 |
| 2011/0169338 | A1* | 7/2011 | Kozakai | H02J 50/12 |
| | | | | 307/104 |
| 2011/0179637 | A1* | 7/2011 | Eberman | H01M 4/582 |
| | | | | 29/623.5 |
| 2012/0202435 | A1* | 8/2012 | Kim | H02J 7/00034 |
| | | | | 455/69 |
| 2012/0274134 | A1* | 11/2012 | Gasparini | H02M 3/1584 |
| | | | | 307/31 |
| 2015/0115726 | A1* | 4/2015 | Kang | H02J 7/025 |
| | | | | 307/104 |
| 2015/0341085 | A1* | 11/2015 | Ettes | H04B 5/0037 |
| | | | | 307/104 |
| 2017/0026209 | A1* | 1/2017 | Lin | H04L 27/24 |
| 2017/0043170 | A1* | 2/2017 | Guardiani | A61N 1/3787 |

OTHER PUBLICATIONS

PCT Written Opinion for PCT Counterpart Application No. PCT/SG20167/050222, 4 pgs. (dated Jul. 14, 2017).
Lee et al., "A Programmable Implantable Micro-Stimulator SoC with Wireless Telemetry: Application in Closed-Loop Endocardial Stimulation for Cardiac Pacemaker," in IEEE Int. Solid-State Circuits Conf. Dig. Tech. Papers, Feb. 2011, pp. 44-45.
Yao et al., "A 20V-compliance implantable neural stimulator IC with closed-loop power control, active charge balancing, and electrode impedance check," in IEEE Asian Solid-State Circuits Conf. Dig. Tech. Papers, Nov. 2014, pp. 201-204.
Cheng et al., "100-channel wireless neural recording system with 54-Mb/s data link and 40%-efficiency power link," in IEEE Asian Solid-State Circuits Conf. Dig. Tech. Papers, Nov. 2012, pp. 185-188.
Lo et al., "A Fully-Integrated High-Compliance Voltage SoC for Epi-Retinal and Neural Prostheses," IEEE Transactions on Biomedical Circuits and Systems, vol. 7, Dec. 2013, pp. 761-772.
Noorsal et al., "A Neural Stimulator Frontend With High-Voltage Compliance and Programmable Pulse Shape for Epiretinal Implants," IEEE Journal of Solid-State Circuits, vol. 47, Jan. 2012, pp. 244-256.

* cited by examiner

SYNCHRONIZED TIME-DIVISION WIRELESS POWER TRANSFER FOR MULTIPLE VOLTAGE APPLICATIONS

CROSS-REFERENCE TO RELATED APPLICATIONS

This patent application is a U.S. National Phase Application under 35 U.S.C. § 371 of International Application No. PCT/SG2017/050222, filed on 20 Apr. 2017, entitled SYNCHRONIZED TIME-DIVISION WIRELESS POWER TRANSFER FOR MULTIPLE VOLTAGE APPLICATIONS, which claims priority from Singapore Patent Application No. 10201603240Y filed on 22 Apr. 2016.

TECHNICAL FIELD

The present invention generally relates to systems and methods for wireless power transfer, and more particularly relates to wireless power transfer systems and methods for implantable medical devices.

BACKGROUND OF THE DISCLOSURE

Wirelessly powered implantable medical devices are under spotlight in recent years both in academic and industry. One of the most important enabling building blocks in such implantable devices is a wireless power management block which receives power through an inductively coupled coil pair to provide power to other functional blocks of the implantable device. Normally a versatile implantable device would require multiple supply voltages for different types of functional blocks such as an analog block, a digital block and a high voltage driver block. The circuit architecture chosen to generate these multiple supply voltages and the power efficiency of this circuit is an important design specification since it greatly affects the overall performance of the implantable device including maximum implantation depth (which is related to the efficiency of the wireless power link) and device form factor (which is related to the number of external components).

Conventionally, there are three topologies to generate multiple supply voltages for wirelessly powered implantable medical device: (a) DC-DC voltage conversion architecture, (b) multiple stage rectifier architecture, and (c) segmental coil architecture. High efficiency DC-DC converters are available to build a high efficiency wireless power management blocks. However, such DC-DC converters require a number of bulky passive components such as inductors, capacitors and/or diodes which require a large form factor for implantable devices utilizing such DC-DC converters. Conventional inductive coupled wireless power transfer topologies are a multiple stage rectifier solution which uses only coupling capacitors, but such coupling capacitors still contribute to a large form factor. Additionally, the power efficiency of such topologies is lower than the DC-DC voltage conversion architecture because of the forward voltage drop on each extra rectifier stage. Conventional segmental coil architectures use a receiver coil having a segmental structure, which is problematic because such segmental coil structures and their resonant matching network are difficult to construct.

Thus, an inductive coupled wireless power transfer topology is needed which overcomes the drawbacks of prior art topologies and provides a wireless power management block for an implantable device which provides a robust power link for improved implantation depth and a minimized device form factor while still providing efficient overall performance of the implantable device. Furthermore, other desirable features and characteristics will become apparent from the subsequent detailed description and the appended claims, taken in conjunction with the accompanying drawings and this background of the disclosure.

SUMMARY

According to at least one embodiment of the present invention, a wirelessly powered implantable medical device receiving time-division wireless power transfer signals is provided. The wirelessly powered medical device includes receiver circuitry for receiving the time-division wireless power transfer signals and a time division switching module. The time division switching module is coupled to the receiver for generating multiple supply voltages in response to the time-division wireless power transfer signals.

According to another embodiment of the present invention, a system for synchronized time-division wireless power transfer is provided. The system includes a wireless transmitter for generating and transmitting time-division wireless power transfer signals and a wirelessly powered device. The wirelessly powered device includes a wireless receiver for receiving the time-division wireless power transfer signals and a time division switching module. The time division switching module is coupled to the wireless receiver and generates multiple supply voltages synchronized to the time-division wireless power transfer signals for powering different circuitry of the wirelessly powered device.

According to a further embodiment of the present invention a method for closed-loop carrier waveform adaption for wireless power control is provided. The method includes generating time-division wireless power transfer signals having a carrier waveform adapted for wireless power transfer and receiving the wireless power transfer signals and generating multiple supply voltages synchronized to the carrier waveform of the wireless power transfer signals. The method further includes generating voltage detection results in response to the multiple supply voltages and adjusting the carrier waveform of the wireless power transfer signals in response to the voltage detection results.

BRIEF DESCRIPTION OF THE DRAWINGS

The accompanying figures, where like reference numerals refer to identical or functionally similar elements throughout the separate views and which together with the detailed description below are incorporated in and form part of the specification, serve to illustrate various embodiments and to explain various principles and advantages in accordance with a present embodiment.

And FIG. 5, comprising

Skilled artisans will appreciate that elements in the figures are illustrated for simplicity and clarity and have not necessarily been depicted to scale.

DETAILED DESCRIPTION

The following detailed description is merely exemplary in nature and is not intended to limit the invention or the application and uses of the invention. Furthermore, there is no intention to be bound by any theory presented in the preceding background of the invention or the following detailed description. It is the intent of the present embodiment to present a synchronized time-division wireless power transfer method and device to achieve both high efficiency and small form factor with simple coil structure particularly designed for use in implantable medical devices.

Figure 1:
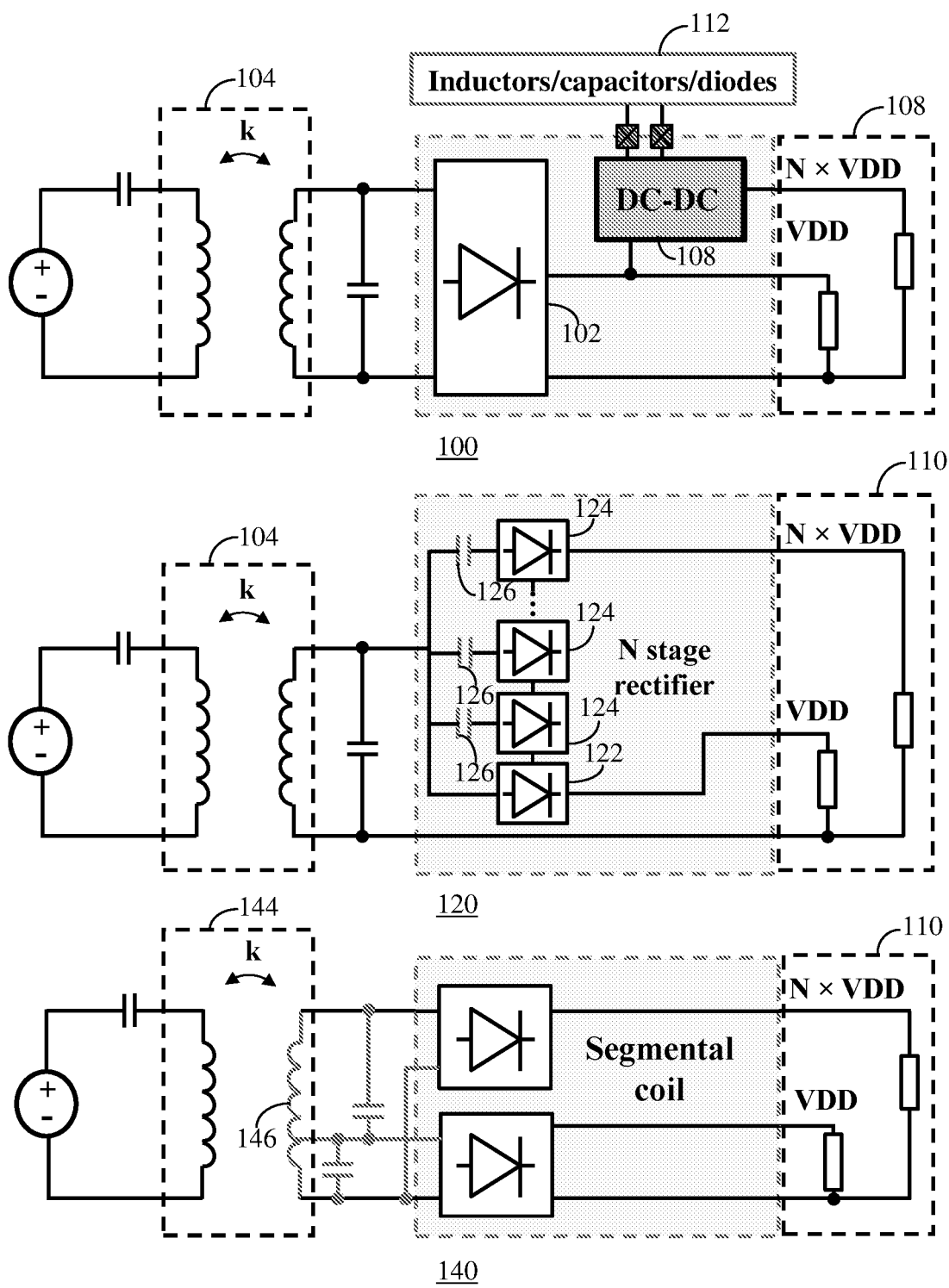
FIG. 1 depicts three diagrams of conventional topologies for generating multiple supply voltages in a wireless power receiver.

Referring to FIG. 1, typical inductive coupled wireless power transfer device diagrams 100, 120, 140 depict three conventional topologies to generate multiple supply voltages for wirelessly powered implantable medical device. As shown in the diagram 100 of a conventional DC-DC voltage conversion architecture, a rectifier 102 is connected with a receiver (RX) coil 104 and converts AC power from the RX coil 104 into a single DC power supply 106. A DC-DC converter 108 is used to generate multiple power supplies 110 from the output of the rectifier 102. High efficiency DC-DC converters are available to build a high efficiency wireless power management block but such DC-DC converters require a number of bulky passive components 112 such as inductors, capacitors and/or diodes, which necessitate large form factors for implantable medical devices incorporating such DC-DC converters.

As shown in the circuit diagram 120 of a conventional multiple stage rectifier solution, a first stage rectifier 122 provides a DC voltage of VDD and N stages rectifiers 124 generate DC voltages of N×VDD to provide the multiple power supplies 110. While only coupling capacitors ($C_1$ to $C_N$) 126 are required for this solution, the coupling capacitors 126 also necessitate a large form factor. Additionally, the power efficiency provided by the multiple stage rectifier solution depicted in the circuit diagram 120 is lower than the power efficiency provided by the DC-DC voltage conversion architecture depicted in the circuit diagram 100 because of the forward voltage drop on each extra rectifier stage.

A conventional segmental coil architecture is depicted in the circuit diagram 140. A RX coil 144 is designed in a segmental structure 146, which is equivalent to two separate inductive coupling coils. Each of the segmental coils is responsible for generating one of the multiple supply voltage 110. The major drawback with the conventional segmental coil architecture is the difficulty to construct the segmental coil structure 146 and its resonant matching network.

Figure 2:
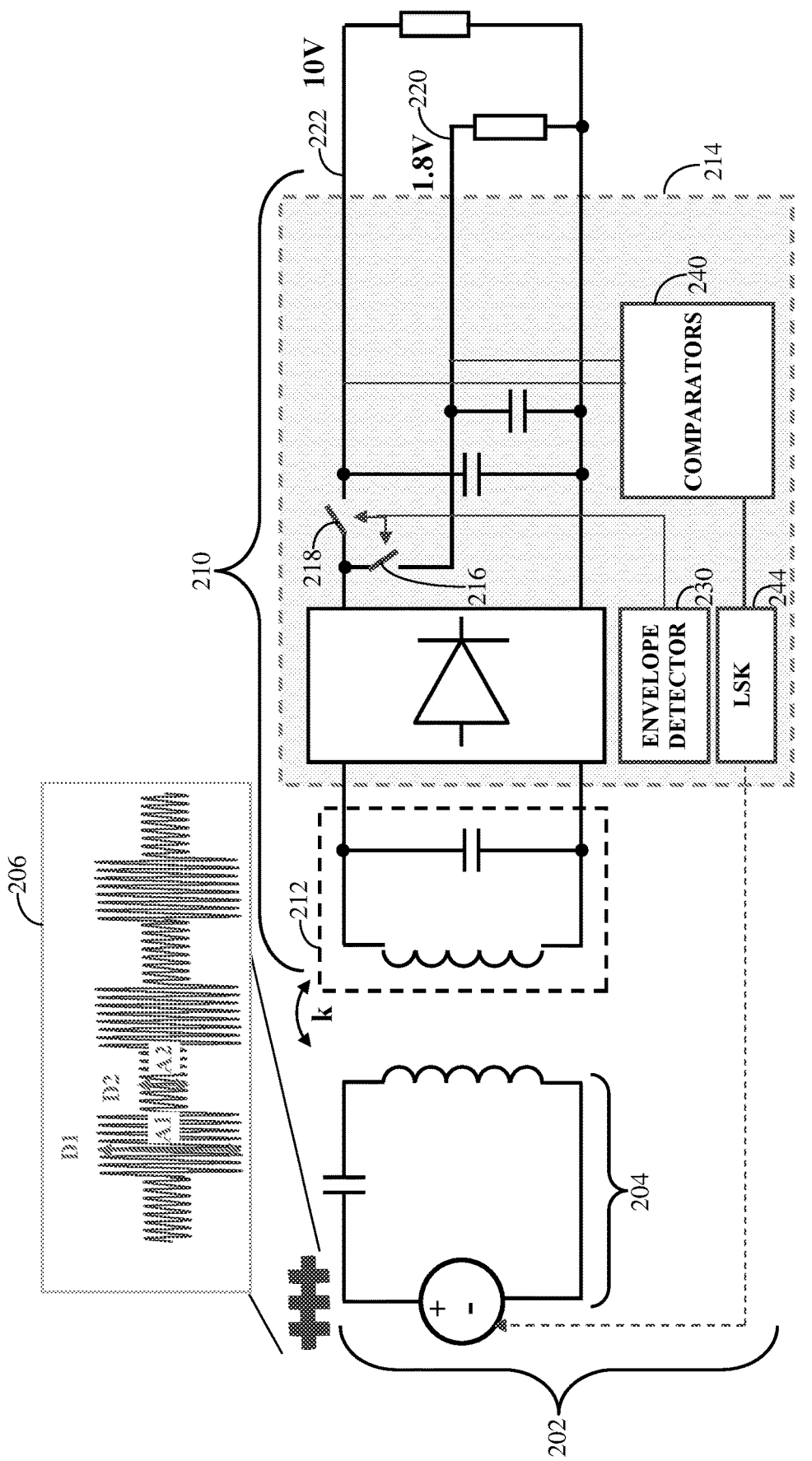
FIG. 2 depicts a diagram of a synchronized time-division wireless power transfer system in accordance with a present embodiment.

Referring to FIG. 2, a diagram 200 depicts a synchronized time-division wireless power transfer system 202 in accordance with a present embodiment. A wireless transmitter 204 generates and transmits time-division wireless power transfer signals 206. A wirelessly powered device 210 includes a wireless receiver 212 for receiving the time-division wireless power transfer signals and a time division switching module 214 for generating multiple supply voltages 216 synchronized to the time-division wireless power transfer signals 206 for powering different circuitry of the wirelessly powered device Instead of using a single power level carrier, the time-division wireless power transfer signals 206 in accordance with the present embodiment uses a multi-level carrier signal to transmit multiple power levels modulated on the carrier of the signals 206. As depicted in the diagram 200, to obtain two supply voltages, two power transfer signals having two power levels (A1 and A2) and duty cycles (D1 and D2) are modulated onto the same carrier. Two switches 216, 218 are used in a single-inductor multiple-output (SIMO) DC-DC converter of the wirelessly powered device 210 to direct the two different power levels to generate different supply voltages 220, 222 (e.g., 1.8V and 10V) for supplying power to different circuitry of the wirelessly powered device 210. The timing of the operation of the switches 216, 218 is synchronized to the power transfer signal modulation on the carrier by using an envelope detector 230 as a switch timing module for control of the switches 216, 218. Thus, in accordance with the present embodiment, two supply voltages can be obtained without requiring multiple passive components (e.g., DC-DC converter 108) in the wireless power receiver 214. Higher efficiency and less number of external components can advantageously be achieved as compared to conventional multiple stage rectifier structures (e.g., rectifiers 122, 124). And, as compared to conventional segmental coil solutions (e.g., segmental coil 146), the wirelessly powered device 210 has simpler coil structure.

In accordance with the present embodiment, the synchronized time-division wireless power transfer system 202 implements closed-loop power control and a comparator 240 is used to sense the voltage value of voltage outputs 220, 222 and generate voltage detection results. The voltage detection results are sent 242 back to the wireless power transmitter 204 through a backscattering (LSK) module 244 to adjust the amplitude (A1/A2) and duty cycle (D1/D2) of the two modulated power levels of the signal 206. In this manner, the synchronized time-division wireless power transfer system 202 advantageously utilizes system level regulation to keep the output voltages 220, 222 to a pre-defined value.

Figure 3:
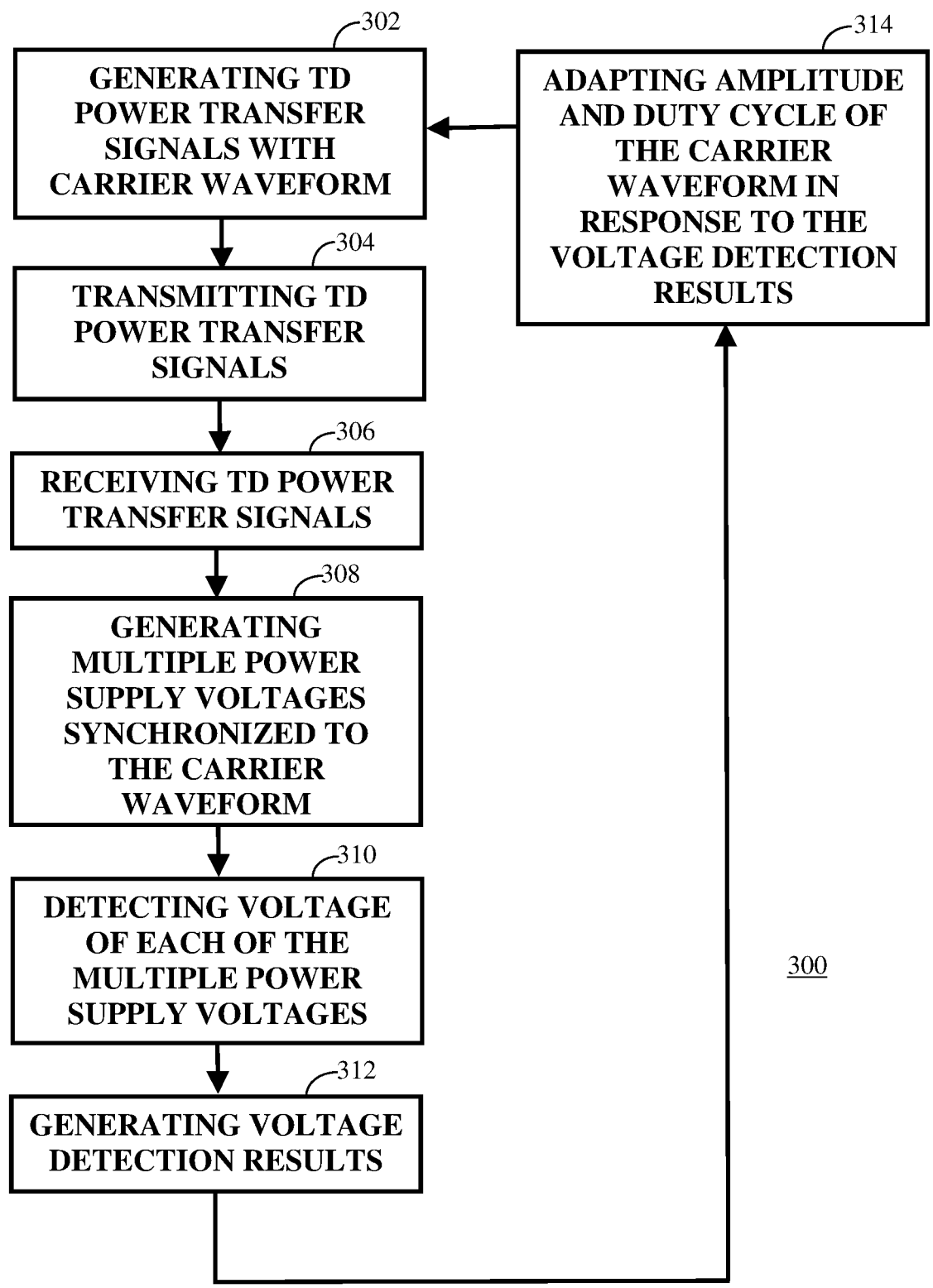
FIG. 3 depicts a flowchart of operation of the closed-loop power control method of the synchronized time-division wireless power transfer system of FIG. 2 in accordance with the present embodiment.

Referring to FIG. 3, a flowchart 300 depicts operation of the closed-loop power control method of the synchronized time-division wireless power transfer system 202 in accordance with the present embodiment. The wireless power transmitter 204 generates 302 the time-division (TD) power transfer signals 206 with a carrier waveform defined by the amplitudes (A1/A2) and the duty cycles (D1/D2). Then, the wireless power transmitter 204 transmits 304 and the wireless receiver 212 receives 306 the time-division (TD) power transfer signals 206. The wireless power receiver 214 generates 308 the multiple power supply voltages 220, 222 synchronized to the carrier waveform. The comparator 240 detects 310 the voltage value of voltage outputs 220, 222 and generates 312 voltage detection results. The voltage detection results are backscattered 313 by the backscattering (LSK) module 244 for the wireless power transmitter 204 to adapt 314 the amplitude (A1/A2) and duty cycle (D1/D2) of the modulated power levels of the signal 206 in response to the voltage detection results. Thus, in accordance with the method and system of the present embodiment, the synchronized time-division wireless power transfer system 202 advantageously utilizes system level regulation to keep the output voltages 220, 222 to a pre-defined value.

Figure 4:
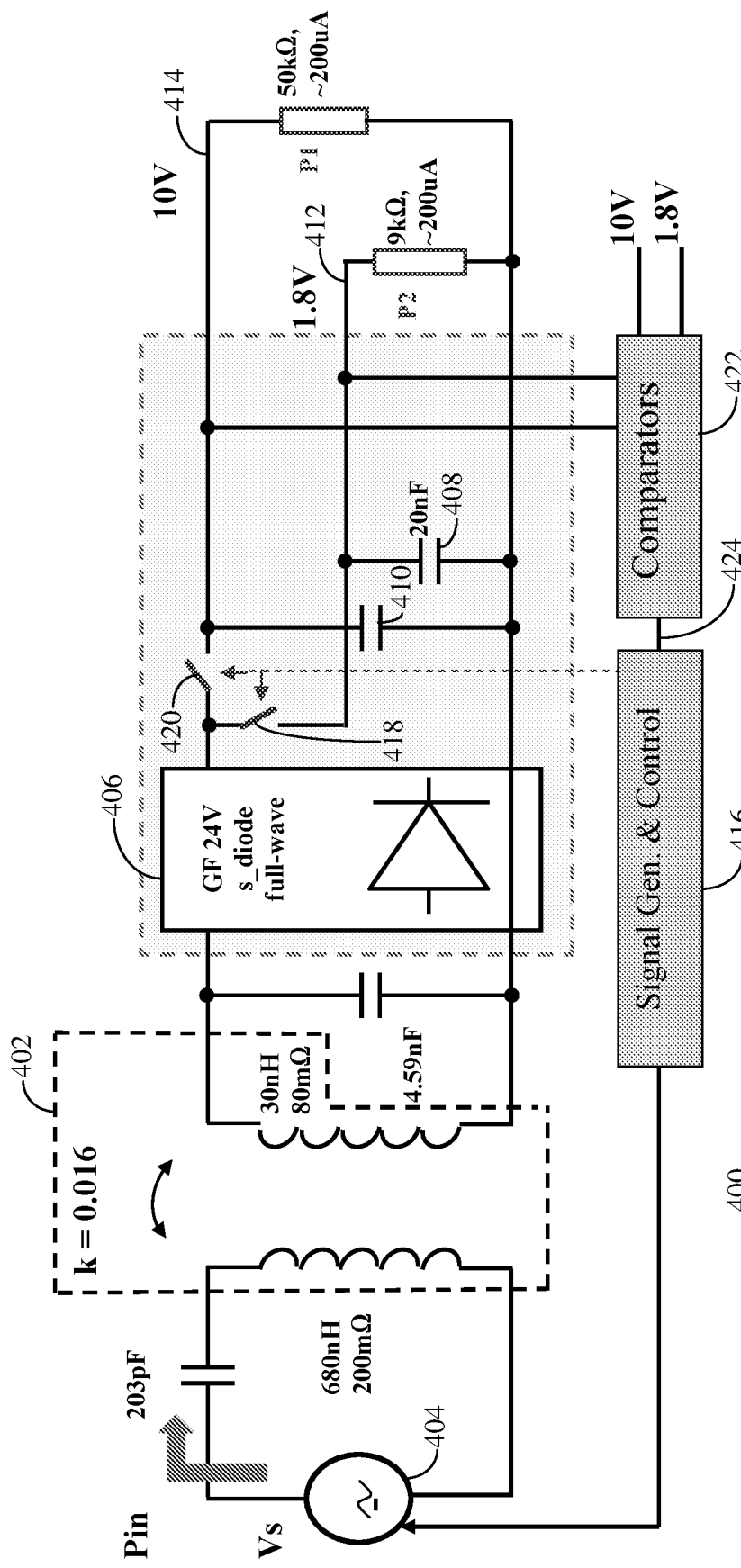
FIG. 4 depicts a diagram of a simulation setup of a synchronized time-division wireless power transfer system in accordance with the present embodiment.

To validate the proposed system and method, a system simulation was performed using a circuit designed in a Global Foundries (GF) 0.18 μm 24V LDMOS process and Verilog-A functional blocks. Referring to FIG. 4, a simulation setup diagram 400 uses an actual coil model 402 and a signal generator 404 generates an input carrier frequency set at 13.56 MHz. A rectifier 406 is designed as a four diode full wave rectifier using a high voltage diode in GF 0.18 μm 24V LDMOS process. All other functional blocks are implemented using Verilog-A.

Two 20 nF capacitors 408, 410 are used as the storage capacitors for 1.8V and 10V outputs 412, 414, respectively. The modulated carrier is generated by an adaptive power amplifier of which the two power levels (A1/A2/D1/D2) are controlled by a digital block 416. The digital block 416 receives a feedback signal from a demodulation block that demodulates backscattered data from the implantable side. On the implant side, an ASK demodulator and a switch timing control block of the digital block 416 are used to control switches 418, 420 to direct different power levels to the storage capacitors 408, 410. The voltages on the storage capacitors 408, 410 are sensed by two simple comparators 422 and the voltage information is backscattered 424 to the external power control block.

In accordance with the present embodiment, the external power transmission block 416 includes an adaptive power amplifier and digital control block to tune carrier parameters A1/A2/D1/D2 to implement the adapting step 314 for the closed-loop power control method in accordance with the present embodiment, thereby enabling a power efficient, simple implant device with small form factor for inductively generating multiple supply voltages.

Figure 5A:
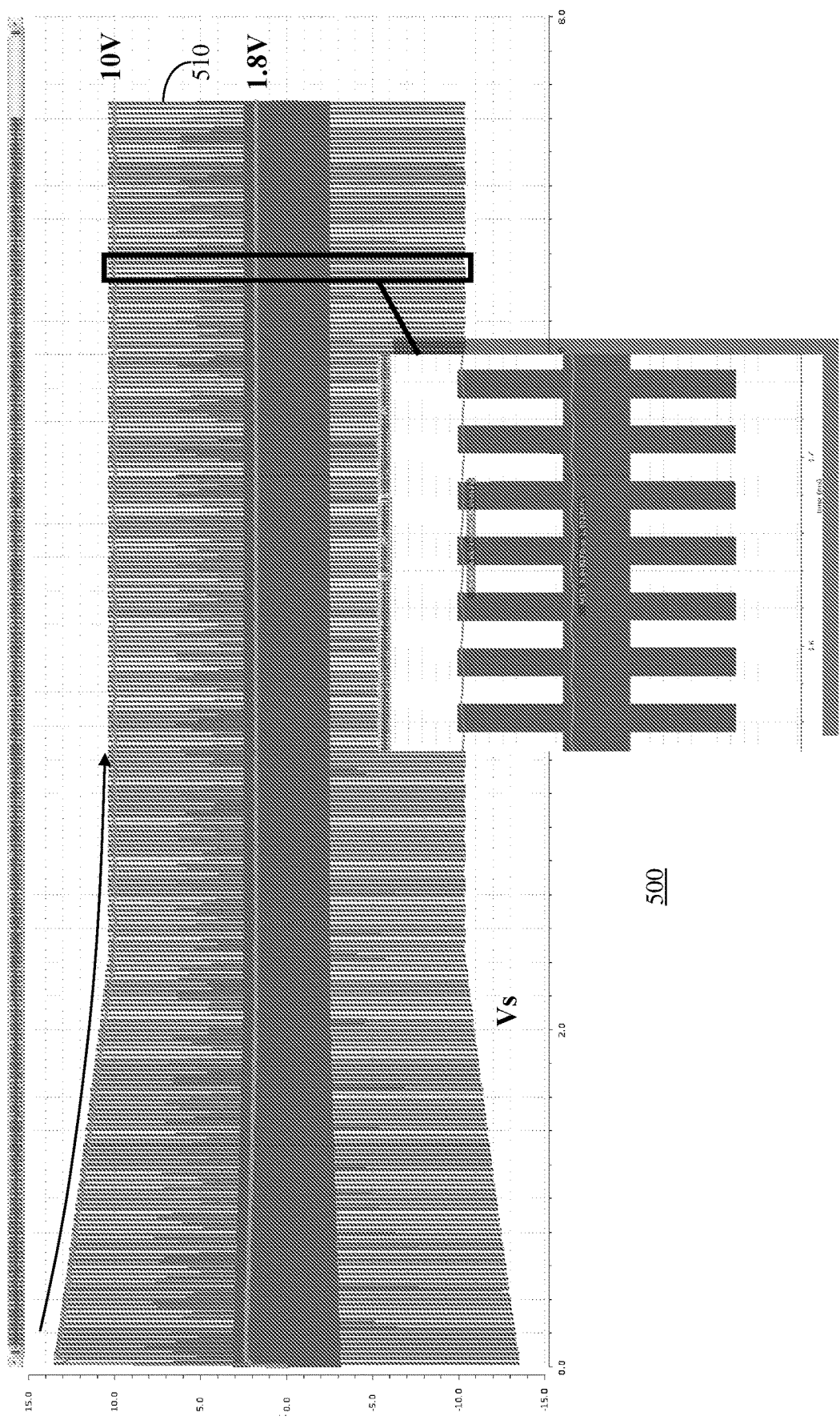
FIGS. 5A and 5B, depicts signaling diagrams of the closed-loop power control method produced by the simulation setup of of FIG. 4 in accordance with the present embodiment.
Figure 5B:
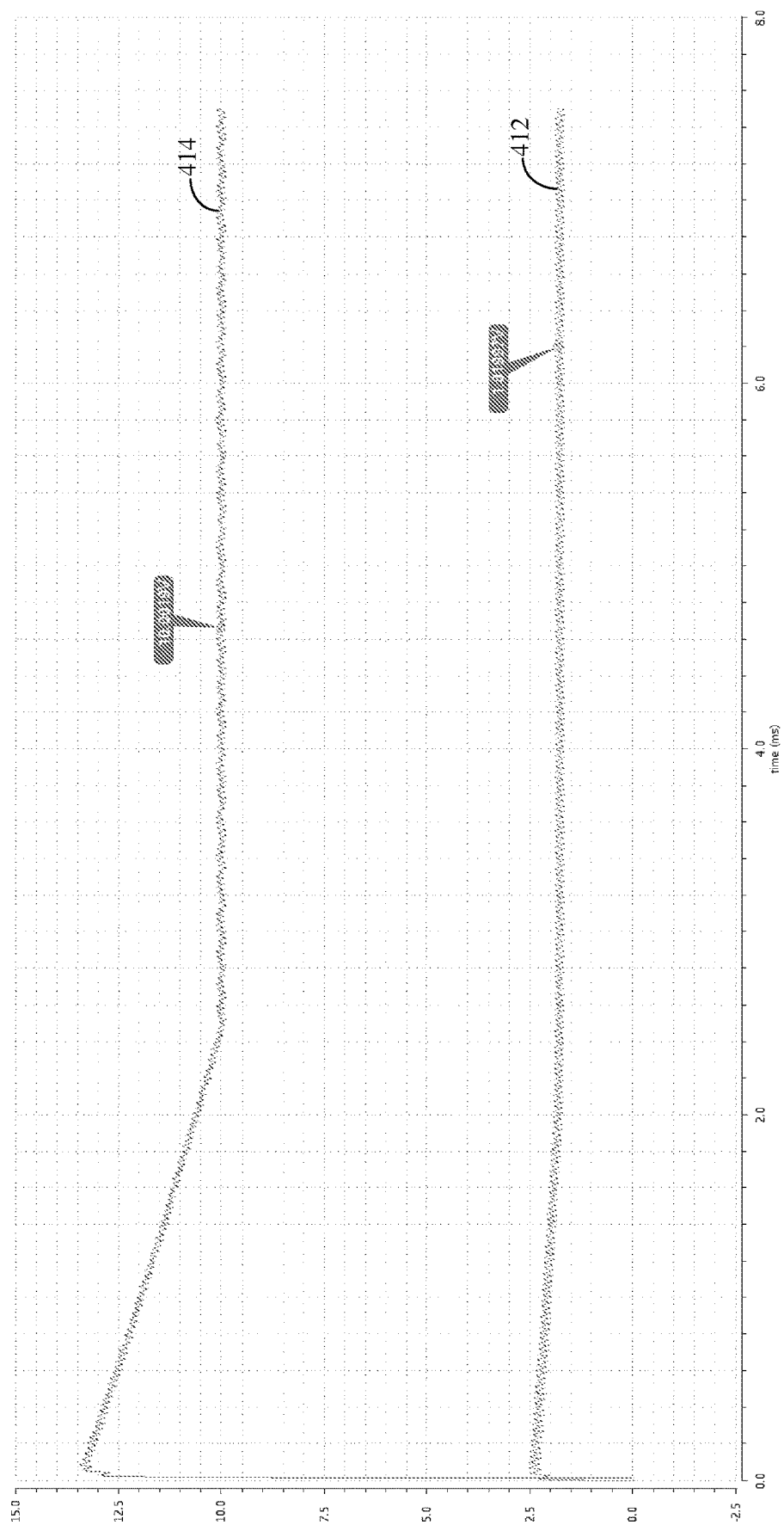

Referring to FIGS. 5A and 5B, signaling diagrams 500, 550 depict the simulation results. The modulated carrier signal 510 is depicted in the diagram 500 and the supply voltages 412, 414 are depicted in the diagram 550. As seen in the diagrams 500, 510, the synchronized time-division wireless power transfer and the proposed closed-loop power control method in accordance with the present embodiment tunes the modulated carrier signal 510 to successfully generate the two supply voltages (1.8V/10V) 412, 414.

Thus, it can be seen that the present embodiment provides a synchronized time-division wireless power transfer method for derivation of multiple supply voltages in the wireless receiver device. The present embodiment advantageously achieves high power efficiency without compromising the form factor and coil design simplicity and provides a wireless receiver device ideal for implantable medical applications.

While exemplary embodiments have been presented in the foregoing detailed description of the invention, it should be appreciated that a vast number of variations exist. It should further be appreciated that the exemplary embodiments are only examples, and are not intended to limit the scope, applicability, operation, or configuration of the invention in any way. Rather, the foregoing detailed description will provide those skilled in the art with a convenient road map for implementing an exemplary embodiment of the invention, it being understood that various changes may be made in the function and arrangement of steps and method of operation described in the exemplary embodiment without departing from the scope of the invention as set forth in the appended claims.

What is claimed is:

1. A wirelessly powered implantable medical device receiving time-division wireless power transfer signals, the wirelessly powered medical device comprising:
   receiver circuitry for receiving the time-division wireless power transfer signals; and
   a time division switching module coupled to the receiver for generating multiple supply voltages in response to the time-division wireless power transfer signals, wherein the time division switching module comprises a single-inductor multiple-output (SIMO) DC-DC converter, and wherein the SIMO DC-DC converter comprises multiple switches for supplying each of the multiple supply voltages to different circuitry of the wirelessly powered implantable medical device, the SIMO DC-DC converter comprising an envelope detector coupled to the multiple switches and configured to synchronize operation of the multiple switches to duty cycles of the time-division wireless power transfer signals for supplying one of the multiple supply voltages to a corresponding one of the different circuitry of the wirelessly powered implantable medical device during a corresponding one of the duty cycles of the time-division wireless power transfer signals having an amplitude corresponding to the one of the multiple supply voltages.

2. The wirelessly powered implantable medical device in accordance with claim 1 wherein the SIMO DC-DC converter further comprises:
   a voltage detector coupled to the multiple switches for detecting the multiple supply voltages and generating voltage detection results; and
   a transmission device coupled to the voltage detector for transmitting the voltage detection results to a wireless transmitter transmitting the time-division wireless power transfer signals for adjusting parameters of the time-division wireless power transfer signals.

3. The wirelessly powered implantable medical device in accordance with claim 2 wherein the parameters comprise the duty cycle of the time-division wireless power transfer signals.

4. The wirelessly powered implantable medical device in accordance with claim 2 wherein the transmission device transmits the voltage detection results to the wireless transmitter by backscattering (LSK).

5. The wirelessly powered implantable medical device in accordance with claim 1 wherein each of the different circuitry of the wirelessly powered implantable medical device operates at a different one of the multiple supply voltages.

6. The wirelessly powered implantable medical device in accordance with claim 3 wherein the parameters further comprise the amplitude of the time-division wireless power transfer signals.

7. A system for synchronized time-division wireless power transfer comprising:
   a wireless transmitter for generating and transmitting time-division wireless power transfer signals; and
   a wirelessly powered device comprising:
      a wireless receiver for receiving the time-division wireless power transfer signals; and
      a time division switching module coupled to the wireless receiver and supplying multiple supply voltages to different circuitry of the wirelessly powered device, wherein the time division switching module is configured to synchronize the supply of the multiple supply voltages to the time-division wireless power transfer signals for powering the different circuitry of the wirelessly powered device, the time division switching module comprising:
      multiple switches for supplying each of the multiple supply voltages to the different circuitry of the wireless receiver; and an envelope detector coupled to the multiple switches for synchronizing the operation of the multiple switches to a duty cycle of the time-division wireless power transfer signals.

8. The system in accordance with claim 7 wherein the time division switching module further comprises a voltage detector coupled to the multiple switches for detecting the multiple supply voltages and generating voltage detection results, the wirelessly powered device further comprising a transmission device coupled to the voltage detector for transmitting the voltage detection results to the wireless transmitter, and wherein the wireless transmitter comprises:
transmitter circuitry for transmitting the time-division wireless power transfer signals; and
a digital block coupled to the transmitter circuitry and configured to adjust parameters of the time-division wireless power transfer signals in response to the voltage detection results for synchronization of the time-division wireless power transfer signals with operation of the multiple switches.

9. The system in accordance with claim 8 wherein the parameters comprise the duty cycle of the time-division wireless power transfer signals.

10. The system in accordance with claim 7 wherein the wirelessly powered device comprises a wirelessly powered implantable medical device and wherein the different circuitry performs various operations of the wirelessly powered implantable medical device.

11. The system in accordance with claim 9 wherein the parameters further comprise an amplitude of the time-division wireless power transfer signals.

* * * * *